United States Patent [19]

Masreliez

[11] Patent Number: 4,527,560
[45] Date of Patent: Jul. 9, 1985

[54] MEDICAL OR DENTAL PROBE WITH SELF-HEATING TIP AND METHODS FOR MAKING

[76] Inventor: Carl J. Masreliez, 3301 181st Pl. Northeast, Redmond, Wash. 98052

[21] Appl. No.: 437,158

[22] Filed: Oct. 27, 1982

[51] Int. Cl.³ .......................... A61B 17/38; A61C 3/00
[52] U.S. Cl. ................. 128/303.1; 219/233; 433/32
[58] Field of Search ............. 128/303.1, 742, 401; 219/233, 235; 433/32

[56] References Cited

U.S. PATENT DOCUMENTS 3,698,394 10/1972 Piper et al. ................... 128/303.1
3,886,944 6/1975 Jamshidi ....................... 128/303.1
4,074,719 2/1978 Semm ........................... 128/303.1
4,392,827 7/1983 Martin .......................... 433/32

Primary Examiner—Lee S. Cohen
Attorney, Agent, or Firm—Seed and Berry

[57] ABSTRACT

A medical or dental probe having a resistive, integrally heated tip. The probe tip provides a nearly continuous, controllable heat, and it may have a narrow, pointed shape. The tip may be heated rapidly, and it provides rapid heating of the instrument, continuous supply of heat for the purpose desired, and concentration of maximum heat at the end of the tip. Methods for making these tips are also described.

15 Claims, 5 Drawing Figures

MEDICAL OR DENTAL PROBE WITH SELF-HEATING TIP AND METHODS FOR MAKING

DESCRIPTION

1. Technical Field

The present invention relates to a medical or dental probe which can deliver continuous heat to a tip, particularly to a narrow, pointed instrument tip.

2. Background Art

In dentistry, narrow, heated tips can be used in root canal therapy when filling the root system with heat-softened gutta-percha (natural rubber) or other substances. Also, a heated instrument is used to build wax replicas of teeth. These replicas are then used for castings via the lost-wax method. A similar method of wax casting is also used in the jewelry industry. In a medical application, a heated tip is often used to seal (cauterize) blood vessels. Many other medical applications are also apparent.

The conventional means for achieving a heated instrument tip today is to heat the tip externally, for example, by holding the tip in a flame or in contact with a resistive heater. The primary disadvantage of this approach is that the instrument tip cools off too rapidly, particularly if the tip is narrow. To achieve the desired degree of heating at the end of the tip, it is often necessary to heat the tip to glowing. This degree of heating increases the risk of accidental burns and tends to rapidly destroy the tip.

Heating of the tip by contact with a resistive heater sometimes involves contacting the tip between an open circuit so that current flows through the tip and thereby heats the tip. This method is disclosed in U.S. patent application Ser. No. 273,906 for a dental instrument heater. Alternatively, the instrument tip may be placed in contact with a resistive heating element so that heat is transferred to the tip by conduction. This method is similar to the common operation of a soldering iron.

A disadvantage of contacting the instrument tip across an open circuit is that sparking of the short circuit may cause "pitting" of the instrument. Also, of course, it is difficult to regulate the temperature of the tip, so the tip may be either overheated or not heated enough. Disadvantages of contacting a resistive heating element include the difficulty of conducting sufficient heat to the end of the instrument tip, particularly if the instrument is narrow. As the heat is conducted along the instrument tip, much of it is radiated and convected away to the surrounding atmosphere. Also, a relatively long time for both the heating and cooling cycles makes the conduction-resistive heater approach undesirable.

DISCLOSURE OF INVENTION

The present invention relates to a medical or dental probe with a self-heating tip and to methods for making these tips. The tip itself is a resistive heating element, thus making rapid heating of narrow and fine instrument tips easily accomplished without pitting. Furthermore, the instrument tip may supply nearly continuous heat through direct resistive heating rather than steadily varying heating through staged heating and cooling cycles. The tip may be properly designed to concentrate the heat at the tip by concentrating the current density in this vicinity.

In one embodiment, an electrically conductive core is surrounded by a nonconductive layer, such as common dielectric insulation. An outer resistive heating layer encircles the core and is electrically connected to the core at a leading end of the core. Current passing through the core and into the resistive layer causes the resistive layer to heat up. The outer resistive layer is preferably constructed so that its cross-sectional perimeter increases as the layer gets farther away from the leading end of the core. A resistive layer of this nature concentrates heating at the tip by increasing the current density at the tip. The tip may also be implemented by a resistive core surrounded by a conductive layer, or the core and outer layer could both be resistive, with the core and outer layer being electrically isolated except at the end.

A second preferred embodiment includes a conductive core on which an insulative layer is deposited by a suitable technique, such as, for example, vacuum depositing, spraying, or anodizing. An outer resistive layer is deposited around the insulation while being connected to the core at its end. Again, as in the first embodiment, the resistive layer is designed to concentrate heating of the resistive layer at the tip.

It is unnecessary that the tip be generally a frustum (i.e., a truncated cone), and instead it may be any desired shape, so long as a conductive element projects to a leading end, where a resistive element is connected to the conductive lead. The resistive element is usually fabricated so that when it heats up, the heat is concentrated at the leading end of the conductor lead. For example, a layered tip may be constructed.

Methods for making self-heating tips and dental probes are also disclosed.

BEST MODE FOR CARRYING OUT THE INVENTION

Figure 1:
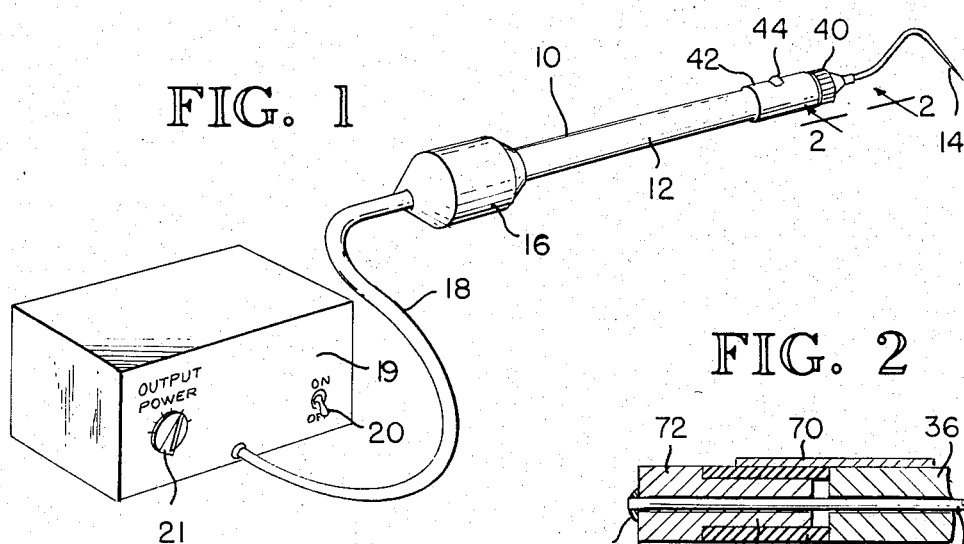
FIG. 1 is an isometric view of a preferred embodiment of the inventive medical or dental probe.
Figure 5:
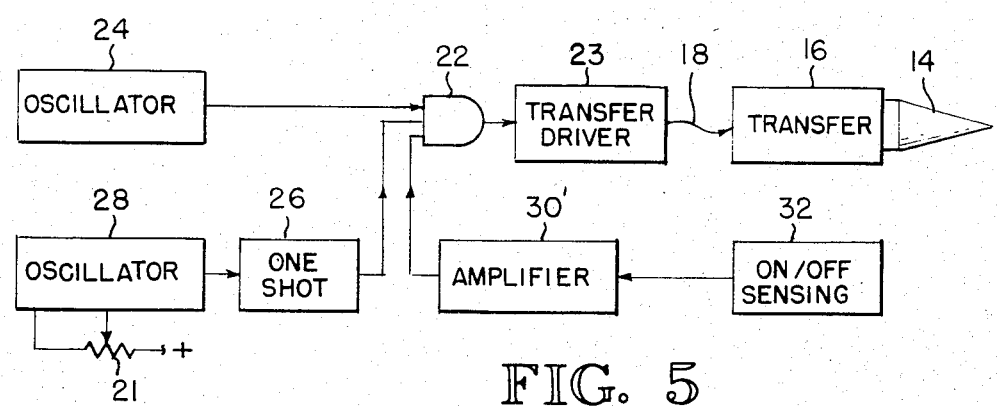
FIG. 5 is a schematic block diagram of the electrical circuitry used to heat the tip.

As shown in FIG. 1, a probe 10 has a base 12 which functions as a handle for the probe 10 and which holds a tip 14, which will be described in more detail. With reference, also, to the schematic of FIG. 5, the rear end of the base 12 includes a step-down transformer 16 having its primary connected to a power cord 18 of the probe 10 to provide electrical power to the tip 14. Use of a transformer within the probe 10 allows the probe cord 18 to carry a relatively small current. The power for the tip 14 may thus be transferred through the cord 18 at a higher voltage and at a lower current so that the transformer 16 may convert this power into a lower voltage/higher current power source, as desired. Power is supplied through the cord 18 by a control unit 19 which is powered either from a wall outlet or by an internal battery. The control unit 19 has a panel on which is mounted an on/off switch 20 and a power control 21. The voltage and current requirements of the tip 14 will vary depending upon its size and desired temperature. However, in one operational embodiment, 10 watts of power are supplied to the tip 14.

The transformer 16 receives power through the probe cord 18 from a transformer driver 23 which may use power transistors or a conventional power amplifier. The driver 23 is capable of supplying sufficient power to heat the tip 14. The transformer driver 23 is energized by the output of an AND-gate 22. The AND-gate 22 receives the output of an oscillator 24, a one-shot 26 (periodically triggered by a second oscillator 28), and the output of an amplifier 30 controlled by an on/off switch 32. When the tip 14 is to be heated, the output of the amplifier 30' is high, as explained hereinafter. Thus, gate 22 is controlled by oscillator 24 and one-shot 26. Oscillator 24 periodically enables the gate 22 at a relatively high frequency, such as about 40 kHz. Oscillator 28 operates at a substantially lower frequency, on the order of 0.5-5.0 Hz. By adjusting the duration of the one-shot 26 with the power control 21 (FIG. 1), the AND-gate 22 can be disabled for an adjustable period of time, thereby adjusting the duty cycle of the gate 22 and hence the power applied to the tip 14. In summary, when the tip 14 is being heated, amplifier 30' enables AND-gate 22 so that the output of the oscillator 24 is gated to the transformer driver 23. However, AND-gate 22 is periodically disabled at a rate determined by the operating frequency of the oscillator 28.

The tip 14 of the probe 10 is curved in the manner common to dental instruments, and it terminates in a point. However, it will be understood that tips 14 of other shapes can be used. The opposite end of the tip 14 is secured to the probe base 12 by a locking cap 40 threaded onto a plastic fitting 42. A metal, touch-sensitive control button 44 is mounted on the fitting 42. When the practitioner grasps the barrel of the base 12 and touches the button 44, a circuit is completed between the base 12 and button 44 through the on/off sensing switch 32 (FIG. 5) which is boosted by amplifier 30 to enable AND-gate 22. A similar touch-control sensor is described in U.S. Pat. No. 4,177,799, which is incorporated herein by reference. Basically, a voltage is applied between the base 12 and button 44. When the practitioner completes the path between the button 44 and base 12, this flow is detected by the on/off sensing circuit 32 to apply a signal to the amplifier 30'.

Figure 3:
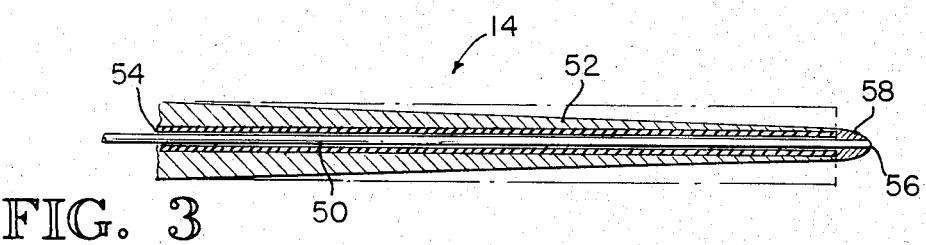
FIG. 3 is a typical longitudinal cross-section of an instrument tip of this invention.

One embodiment of the probe tip 14 is shown in FIG. 3. A copper wire 50 runs inside a hollow core 52 of the tip 14. The wire 50 is surrounded by a layer of substantially nonconductive (insulative) material 54, except for a small portion near the leading end 56 of the wire 50. At this leading end 56, a stainless steel outer layer 58 is soldered to the wire 50 to provide an electrical coupling between the wire 50 and the outer layer 52. The outer layer 52 is substantially isolated and disconnected from the wire 50 except at the leading end 56. Current is carried through the wire 50 to the leading end 56, where it enters the outer layer 52. Because the outer layer 52 has a resistance greater than that of the inner wire 50, the outer layer 52 forms a resistive heater for the tip 14. Preferably, the outer layer 52 forms a hollow core so that the cross-sectional area of the outer layer 52 increases as the layer proceeds away from the leading end 56. An outer layer 52 of this nature thus has a generally decreasing current density away from the end 56, and, therefore, provides more heat near the leading end than farther away from the leading end 56. Therefore, the greatest heat may be concentrated at the tip of the instrument probe.

Figure 4:
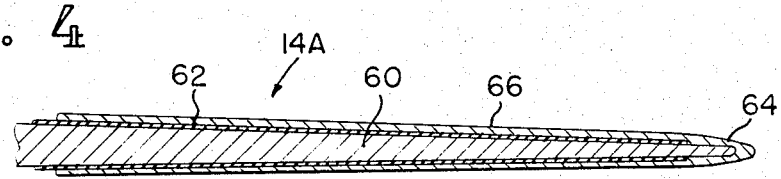
FIG. 4 is a longitudinal cross-sectional view similar to FIG. 3 showing a second preferred embodiment of a tip of this invention.

FIG. 4 shows an alternate embodiment of a preferred tip of this invention. The alternate tip 14A includes an aluminum core 60 having an insulation layer 62 fabricated about it. The leading end 64 of the aluminum core 60 has the insulative layer removed from it. At this end, a resistive outer layer 66 is in electrical contact with the core 60. This outer layer 66 is similar to the outer layer 52 of the first embodiment. That is, it is a resistive element which heats up when current passes through the core into the outer layer. It may be shaped to provide concentrated heating near the leading end 64 of the alternate tip 14A. For example, the outer conductive layer 66 may be a metal deposited by vacuum deposition or flame spraying.

Because the method of construction of a tip of the nature shown in FIG. 4 allows for fabrication in nearly any shape, this method may be preferred. That is, the tip can be made by fashioning the core 60 into the desired shape. The core 60 is then processed to provide the insulative layer 62 between the conductive core 60 and resistive outer layer 66. The outer layer 66 may then be deposited upon the insulative layer 62 to make electrical contact with the core 60 at or near the leading end 64. Almost any shape of tip may be employed with this method; and, particularly, very narrow, fine point tips may be fabricated to include an integral resistive heating element. The thickness of the outer layer 66 may be readily controlled to provide the desired heat concentration near the leading end 64 of the tip 14A.

Figure 2:
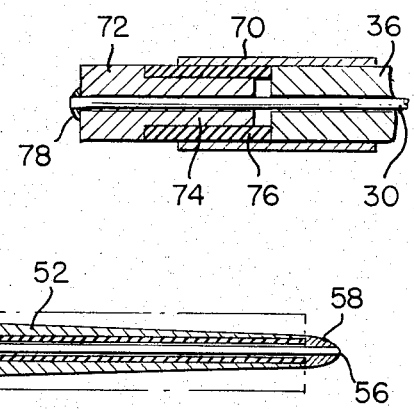
FIG. 2 is a cross-sectional view of the tip/probe interface.

The interface between the tip 14 and probe base 12 is illustrated in FIG. 2 for the tip 14 of FIG. 3. A tubular, electrically conductive collar 70 of brass or the like surrounds and makes electrical contact with the end of the outer layer 36. The end of the collar 70 extends beyond the end of the outer layer 36 to form a cylindrical recess. A conductive tube 72, having a reduced diameter projection 74 surrounded by a layer of insulation 76, fits into the cylindrical recess formed by the collar 70. The outer layer 36 is thus supported from the tube 72, but is electrically insulated from it. The wire 30 extending through the hollow interior of the outer layer 36 extends through a hollow cavity in the tube 72 and is soldered to the end of the tube 72 at 78. The collar 70 and tube 72 thus form contact points for completing a circuit through the outer layer 36 and wire 30. The tube 72 and collar 70 are inserted through the cap 40 into the fitting 42. The collar 70 makes contact with the cap 40 and, from there, to one contact of the transformer 16. The tube 72 abuts a contact in the fitting 42 and is connected to the other terminal of the transformer 16. In this manner, tips 14 can be removed for sterilization and then re-attached to the probe 10 by merely releasing the cap 40 and inserting the substitute tip 14.

While preferred medical or dental probes have been described along with their methods of construction, those skilled in the art will readily recognize modifications that may be made to the embodiments disclosed. For example, the core 60, instead of the outer layer 66, could be fabricated from a resistive material, and vice versa; or the same material could be used in both core 60 and outer layer 66. These modifications are intended to be a part of the invention if they use the underlying concepts of this invention. The claims of this invention should be interpreted to the extent allowable by reference to this description and to the prior art. The preferred embodiments disclosed should be used by way of limitation only to the extent necessary to define the invention. Specifically, the resistive outer layer 52 or 66 may be of uniform cross-sectional area if heat concentration at the tip is not desired. Also, the tip may assume a variety of shapes other than the shape shown herein. For example, a tubular tip may be flattened to a trowel-like configuration and the flattened tip may be formed into a spoon.

I claim:

1. A medical and dental probe comprising:
   a probe base;
   a tip projecting from said base, said tip having an inner conductive core member and an outer layer of resistive material surrounding said core member, said outer layer having a cross-sectional area along its length gradually decreasing toward a distal end of said tip to increase the electrical current density in said outer layer toward said distal end upon passage of electric current, said core member and outer layer being connected to each other at the distal end of said tip and electrically isolated from each other along the remaining portion of said tip, the series combination of said core member and outer layer having a relatively high resistance and creating a lengthwise temperature gradient in said outer layer increasing toward said distal end; and
   means for passing an electric current between said core member and said outer layer away from the distal end of said tip, thereby causing current to flow through said outer layer and said core member to heat said tip.

2. The probe of claim 1 wherein said outer layer has a thickness tapering lengthwise toward said distal end of the tip.

3. The probe of claim 1 wherein said core member is a conductor of substantially uniform cross-sectional area and said outer layer is a body of resistive material surronding said conductor and insulated therefrom except at the distal end of said tip, said outer layer of resistive material having a tapering layer thickness that decreases toward the distal end of said tip, thereby decreasing the cross-sectional area of said resistive material toward said distal end.

4. The probe of claim 3 wherein said outer layer has a longitudinal opening at said distal end receiving said conductor therein for electrical connection of said conductor to said outer layer.

5. The probe of claim 1 wherein said core member is a conductor having a cross-sectional area that decreases toward the distal end of said tip, and wherein said outer layer is a body of resistive material of substantially uniform thickness surrounding and substantially conforming to the shape of said conductor, said outer layer being insulated from said conductor except at the distal end of said tip, whereby the cross-sectional area of said resistive material decreases toward said distal end to increase the electrical current density in said outer layer toward said distal end.

6. The probe of claim 5 wherein said conductor is at least partially surrounded by an insulator and wherein said resistive material is vacuum-deposited onto said insulator.

7. The probe of claim 5 wherein said conductor has a generally conical shape, said outer layer being supported along a substantial portion of its length by said conductor with a layer of insulating material therebetween except at said distal end of said tip.

8. An instrument tip for a medical and dental probe, comprising:
   an inner conductive core defining the general shape of the tip and adapted to carry current to a leading end of the core; and
   an outer layer of resistive material encircling the core along a substantial length thereof, said outer layer being substantially electrically insulated and disconnected from the core except for an area adjacent the leading end of the core, said outer layer having a distal end portion with a cross-sectional area gradually increasing along the length of said tip in a direction away from the leading end, the series combination of said core and outer layer having a relatively high resistance so that said tip is adapted to heat up when an electric current passes through the core and outer layer, with the heat generated being concentrated near the leading end of said tip.

9. The instrument tip of claim 8, further comprising a substantially nonconductive element disposed between the core and outer layer so that the outer layer is substantially electrically insulated and disconnected from the core except for the area adjacent the leading end.

10. The instrument tip of claim 8 wherein the resistive outer layer is generally a conical shell, the tip of the conical shell is positioned substantially at the leading end of the core, and the conical shell has an interior cavity receiving said inner conductive core.

11. A dental instrument hot probe having an electrically heated tip, comprising:
    an elongated base adapted to serve as a handle for the probe;
    a tip extending from one end of the base, said tip having a leading end configured for use as a dental probe; and
    means for heating the tip by direct resistive heating so that the tip heats up by passing an electric current through the tip, the tip including a pair of coaxially disposed elements substantially electrically isolated and disconnected from each other except for an area adjacent their leading ends, an outer one of said coaxial elements having a relatively high resistance and a cross-sectional area that gradually increases along the length of said tip in a direction away from the leading end of the tip to create a lengthwise temperature gradient with heat concentrated near the leading end of said tip.

12. An electrically heated instrument tip for a medical and dental probe, comprising the product made by the process of:
    shaping a conductive core into the desired shape for the tip, the core having a leading end;
    placing an insulative layer around the core; and
    electrically coupling an outer resistive element to the core so that the element encircles the insulative layer and is substantially isolated and disconnected from the core except at the leading end, the series combination of said core and outer element having a relatively high resistance so that the tip is adapted to heat up when an electric current passes through the core and element, said outer element having a cross-sectional area gradually decreasing along the length of said core toward said leading end to increase the electrical current density in said outer element toward said leading end upon passage of electric current.

13. The tip of claim 12 wherein the core is aluminum or an aluminum alloy.

14. The tip of claim 12 wherein electrically coupling the element to the core includes vacuum depositing the element over the insulated core.

15. The tip of claim 12 wherein electrically coupling the element to the core includes flame spraying the element over the insulated core.

* * * * *